United States Patent
Lin

(12) 
(10) Patent No.: US 8,337,708 B2
(45) Date of Patent: Dec. 25, 2012

(54) METHOD FOR MANUFACTURING GREEN-ENERGY WATER AND DEVICE THEREOF

(75) Inventor: Tien-Tsai Lin, Taipei (TW)

(73) Assignee: S.A.W. Green Technology Corporation, Taipei County (TW)

( * ) Notice: Subject to any disclaimer, the term of this patent is extended or adjusted under 35 U.S.C. 154(b) by 456 days.

(21) Appl. No.: 12/640,003

(22) Filed: Dec. 17, 2009

(65) Prior Publication Data

US 2011/0150751 A1    Jun. 23, 2011

(51) Int. Cl.
*C01B 5/00* (2006.01)
*B01J 19/00* (2006.01)

(52) U.S. Cl. .............. 210/748.09; 210/763; 210/748.01; 210/767; 210/243; 422/162; 422/182; 422/211; 422/29; 422/186; 423/580.1; 423/645; 426/66; 204/155; 204/157.15; 204/157.5; 204/157.52; 204/660; 204/664

(58) Field of Classification Search .................. 210/639, 210/641, 650, 758, 806, 764, 259, 202, 748.01–748.2, 210/749, 209, 198.1, 138, 222, 226, 85, 695, 210/605, 763, 767, 129, 243; 204/155, 157.15, 204/157.5, 157.52, 557, 660, 450, 664; 426/66; 423/580.1, 645; 422/186.01, 186; 205/571
See application file for complete search history.

(56) References Cited

U.S. PATENT DOCUMENTS

| | | | | |
|---|---|---|---|---|
| 5,130,031 | A * | 7/1992 | Johnston | 210/748.04 |
| 5,736,055 | A * | 4/1998 | Cooper | 210/748.1 |
| 6,468,428 | B1 * | 10/2002 | Nishii et al. | 210/497.3 |
| 6,524,447 | B1 * | 2/2003 | Carmignani et al. | 210/748.11 |
| 2006/0275355 | A1 * | 12/2006 | Bagley | 424/450 |
| 2010/0062261 | A1 * | 3/2010 | Chang et al. | 428/426 |

* cited by examiner

*Primary Examiner* — Joseph Drodge
*Assistant Examiner* — Cameron J Allen
(74) *Attorney, Agent, or Firm* — Leong C. Lei

(57) ABSTRACT

A method for manufacturing green-energy water, including: conducting water flow through a self-support visible-light photocatalytic reaction device, which decomposes the water into hydrogen ions and hydroxide ions; conducting the hydrogen ions and the hydroxide ions through an ion separation device, which separates the hydrogen ions and the hydroxide ions from each other; and conducting the separated hydroxide ions into an amount of water to form an amount of alkaline green-energy water and conducting the separated hydrogen ions into another amount of water to form an amount of acidulous green-energy water. The green-energy water manufactured in this way is environmentally friendly and can be used in cleaning purposes of photoelectric and semiconductor industries, processing of waste water, organic cultivation, organic agriculture, purification of water, sterilization of medical facility.

10 Claims, 5 Drawing Sheets

METHOD FOR MANUFACTURING GREEN-ENERGY WATER AND DEVICE THEREOF

(a) TECHNICAL FIELD OF THE INVENTION

The present invention generally relates to a manufacturing method, and more particularly to a method for manufacturing green-energy water and a device thereof; wherein a self-support visible-light photocatalytic reaction device decomposes water to $H^+$ ions and $OH^-$ ions, wherein since water is a polar solvent, the products of the reaction become ionic groups, which can be efficiently separated into $H^+$ ions and $OH^-$ ions by an electrical field and wherein the separated $H^+$ ions and $OH^-$ ions are dissolved in water to form a green-energy water that contains $H_3O_2^-$ or $H_3O^+$.

(b) DESCRIPTION OF THE PRIOR ART

In the current technology for generation of green-energy water, the green-energy water is often produced through electrolysis. In the process of electrolysis, an electrolyte, such as sodium chloride (NaCl), must be added in water, and then electricity is applied to generate functional water of acidulous water and/or alkaline water. The pH value of the functional water is dependent on the contents of sodium hydroxide, hypochlorous acid, and/or sodium hypochlorite in the water. In other words, the functional water contains the ions of the above mentioned sodium hydroxide and the likes and thus the functional water cannot become pure water that contains only $H_2O$ is completely free of other ions.

Currently, a method that generates peroxide ions by adding photocatalysts in water to induce oxidation-reduction reaction is available. The peroxide ions has a oxidizing power stronger than chlorine and ozone and can decompose harmful substance that cannot be decomposed by chlorine and ozone so that it can generate pure water. Such best pure water is the green-energy water. However, direct application of photocatalysts in this way cannot achieve the effect of photocatalysts and the reason is that when the photocatalysts show the same polarity in water, they cannot separate electrons and holes, leading to extremely poor efficiency and incapability of fully exploiting the effect thereof, whereby they cannot provide industrial effectiveness.

Further, addition of ozone provides certain efficacy of purification and sterilization of water. Ozone has activation energy of 74.1 Kcal/mole, which is effective in killing organisms or bacteria, but is not so effective for complete decomposition. For example, colon bacteria can be oxidized by ozone to become endotoxin. Although colon bacteria are killed but the oxidation of colon bacteria to generate endotoxin is a source of fever for human body. Thus, the removal of organisms is only good for oxidization and full decomposition of the organisms is generally not possible, making it difficult to generate pure functional water.

The following table gives a comparison of advantages/disadvantages among energy-contained green-energy water, electrolysis functional water, and ozone functional water that are produced with the conventional ways.

| property | green-energy water | electrolysis functional water | ozone functional water |
|---|---|---|---|
| pH value | acid or alkali | acid or alkali | acid |
| activation energy | 120 Kcal/mole | 30 Kcal/mole | 74.1 Kcal/mole |
| organism decomposition capability | best | second best | good |
| stain removal capability | best | second best | good |
| secondary pollution | no | chemical residuals | no |
| energy consumption | low | high | intermediate |
| addition of chemicals | no | electrolyte | oxygen |

SUMMARY OF THE INVENTION

An object of the present invention is to provide a method for manufacturing green-energy water and a device thereof, wherein a self-support photocatalyst is formed by being attached to a substrate formed of a metallic conductor having a mesh structure by employing vacuum coating, being "self-support" meaning the photocatalyst is attached and fixed to a substrate with application of fastening components, such as adhesives, so as to allow the photocatalyst to be attached to a substrate without being decomposed, and wherein a light source is provided and a reaction environment having a temperature of less than 100° C. is provided, in which the mesh structure to which the photocatalyst is attached is grounded for fast separation of electrons and holes and thus improving the efficiencies of catalyzed photoreaction and sensitized photoreaction of the photocatalyst.

A second object of the present invention is to provide a method for manufacturing green-energy water and a device thereof, wherein an ion separation device is provided for fast separation of $H^+$ ions and $OH^-$ ions by applying an electric field and a magnetic field to attract positive and negative ions, so as to reduce re-combination rate of the $H^+$ ions and $OH^-$ ions and improve productivity.

A third object of the present invention is to provide a method for manufacturing green-energy water and a device thereof, wherein emulsification induced by ultrasonic waves and cavity effect are employed to provide a pulling force applied to the $H^+$ and $OH^-$ ions by vacuum effect to prevent spillage and emulsification is employed to cause dissolution of the ions in water to form high concentration green-energy water.

A fourth object of the present invention is to provide a method for manufacturing green-energy water and a device thereof; wherein a reduced temperature is used to lower the activity of the ions in order to extend the lifespan of the ions and increase the concentration of the green-energy water.

A fifth object of the present invention is to provide a method for manufacturing green-energy water and a device thereof; wherein high concentration $H_3O_2^-$ green-energy water is used, which comprises an electrically negative, alkaline aqueous solution, which shows excellent result for decomposing organic substances, and which helps preventing oxidization of metal due to carrying negative electricity, so as to be used in cleaning operation and handling total organic carbon (TOC) of waste water.

A sixth object of the present invention is to provide a method for manufacturing green-energy water and a device thereof; wherein high concentration $H_3O^+$ green-energy water is used, which comprises an electrically positive, acidulous aqueous solution, which shows excellent result for sterilization, deodorization, and decomposition of metal, and which helps removing oxidization of metal due to carrying positive electricity, so as to be used in deodorization, sterilization, washing of metal or metal ions.

To achieve the above objects, the present invention provides a method for manufacturing green-energy water, comprising:

Conducting water flow through a self-support visible-light photocatalytic reaction device, which decomposes the water into $H^+$ ions and $OH^-$ ions; conducting the $H^+$ ions and the $OH^-$ ions through an ion separation device, which separates the hydrogen ions and the hydroxide ions from each other; and conducting the separated hydroxide ions into an amount of water to form an amount of alkaline green-energy water and conducting the separated hydrogen ions into another amount of water to form an amount of acidulous green-energy water.

To achieve the above objects, the present invention provides green-energy water manufacturing device comprising: a self-support visible-light photocatalytic reaction device; and an ion separation device coupled to the self-support visible-light photocatalytic reaction device.

The above green-energy water manufacturing device further comprises an ion emulsification device, which is connected to the ion separation device and comprises an ultrasonic wave emission source for emulsifying the ions.

The above-mentioned self-support visible-light photocatalytic reaction device comprises: a visible-light photocatalyst board; a heater, a light source, and a grounding line.

The above-mentioned ion separation device comprises: an electric field, which is supplied with a direct current and has an inlet end, an outlet end, a positive electrode board, and a negative electrode board opposite to the positive electrode board; an ion separation plate, which is set between the positive and negative electrode boards; and two conveyance tubes, which are connected to the outlet end of the ion separation device and are respectively located at opposite sides of the ion separation plate.

The above-mentioned separation device comprises: an electric field, which is supplied with a direct current and comprises a positive electrode board and a negative electrode board opposite to the positive electrode board; a magnetic field, which is set parallel to the electric field and comprises an N magnetic pole and an S magnetic pole; an ion separation plate, which is set between the positive and negative electrode boards; and two conveyance tubes, which are respectively located at opposite sides of the ion separation plate for respectively conveyance of the $H^+$ ions and $OH^-$ ions.

The hydroxide ions that are separated by the ion separation device are conducted through a Venturi tube that is connected to the ion separation device into the ion emulsification device and the ultrasonic wave emission source of the ion emulsification device emits ultrasonic waves to the hydroxide ions to cause emulsification and thus fast dissolution of the hydroxide ions into water to thereby form high concentration alkaline green-energy water. The water conducted into the Venturi tube is cooled by a water cooling device to have temperature of the water controlled within a range between freezing point and room temperature.

The visible-light photocatalyst board comprises a metal mesh.

The heater is a heating device selected from a group consisting of electrical resistance heater, infrared heater, and thermal electron heater.

With the above discussed techniques, the present invention, which is provided to overcome the drawbacks of the conventional ways of application of photocatalysts in green-energy water, shows the following advantages:

(1) The present invention expands the absorption range of light by the photocatalyst from ultraviolet to visible light and this improves the utilization of photo energy and thus increases the productivity of green-energy water.

(2) The present invention provides an ion separation device, which realizes separation of ions by applying a magnetic field or an electric field to attract the ions in order to prevent reversed reaction and improve efficiency so that the conventional problem that the decomposed water molecules may easily induce reversed reaction due to accumulation of energy is effectively overcome.

(3) The present invention provides an adhesive-free self-support technology for photocatalysts, which replaces the conventional adhesive-bonding carrier, so that the lifespan of substrate can be extended in the operation of generation of green-energy water.

(4) The present invention provides a $\Delta G>0$ reaction mechanism for decomposition of water by the photocatalyst, which is advantageous to conduct out the gaseous $OH^-/H^+$ ions formed by decomposition of water, so as to improve productivity of green-energy water.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
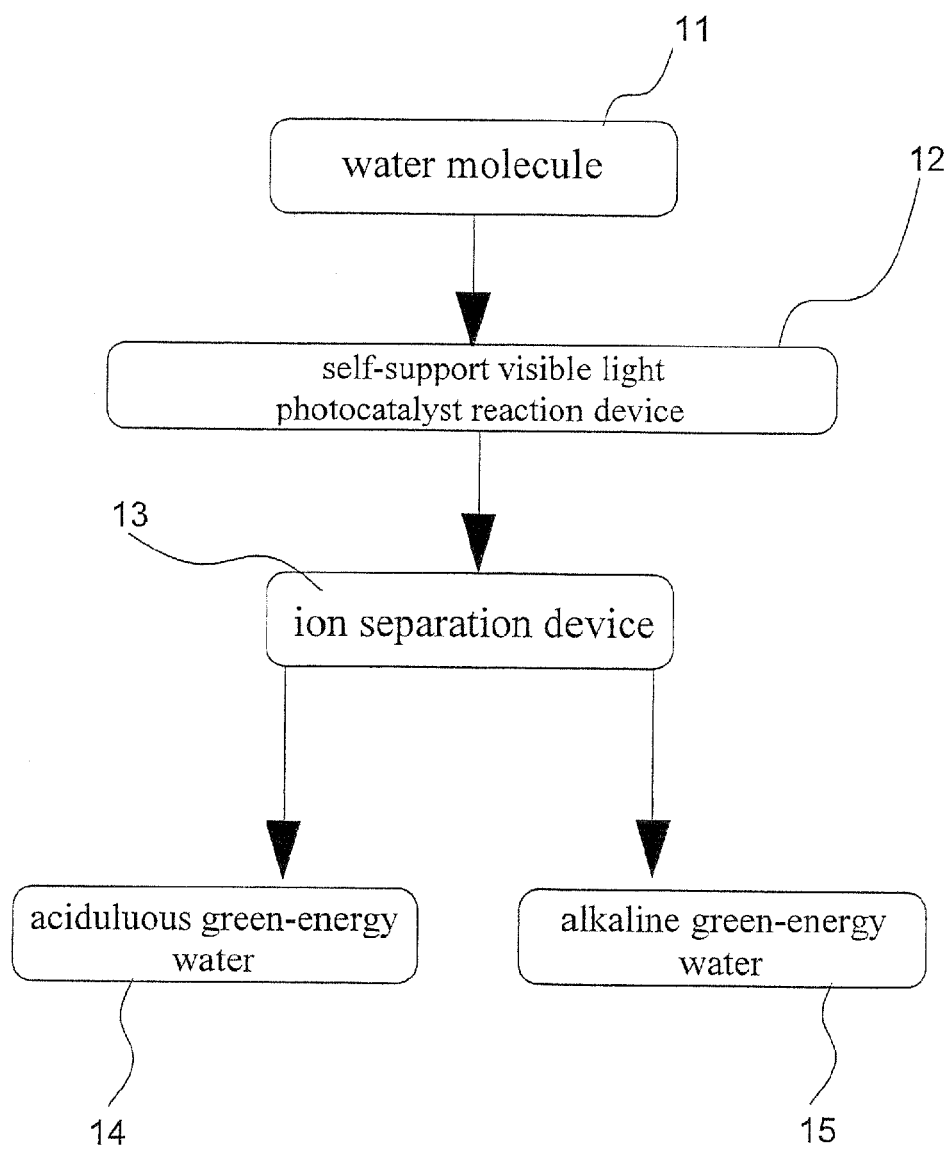
FIG. 1 shows a flow chart of a method for manufacturing green-energy water in accordance with the present invention.
Figure 3:
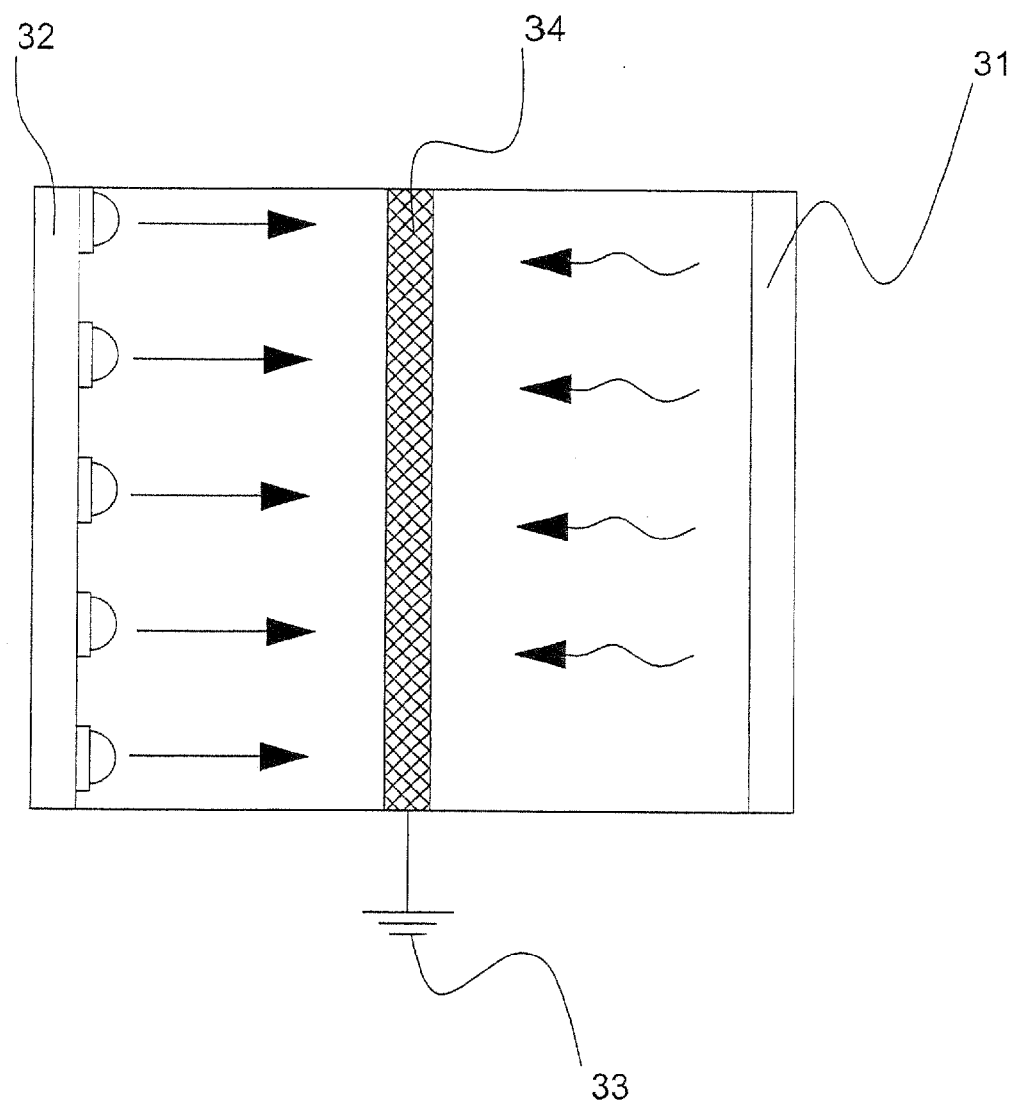
FIG. 3 shows a schematic view of a self-support visible-light photocatalytic reaction device in accordance with the present invention.

Reference is now made to FIG. 1 of the attached drawings, and an illustration of a method for manufacturing green-energy water in accordance with the present invention will be given. The method of the present invention comprises the following steps:

(a) Water molecules are conducted to flow through a self-support visible-light photocatalytic reaction device, as shown in FIG. 3. The self-support visible-light photocatalytic reaction device comprises a visible-light photocatalyst board 34, which carries out the reaction of decomposing water ($H_2O$) into hydrogen ion ($H^+$, which is also referred to as "H ion" herein) and hydroxide ion ($OH^-$, which is also referred to as "OH ion" herein). The visible-light photocatalyst board 34 is formed of a substrate made of metallic conductor and in a preferred embodiment of the present invention; the substrate comprises a metal mesh structure. The substrate has a surface on which $TiO_xN_{1-x}$ is coated to make the visible-light photocatalyst board 34.

Figure 4:
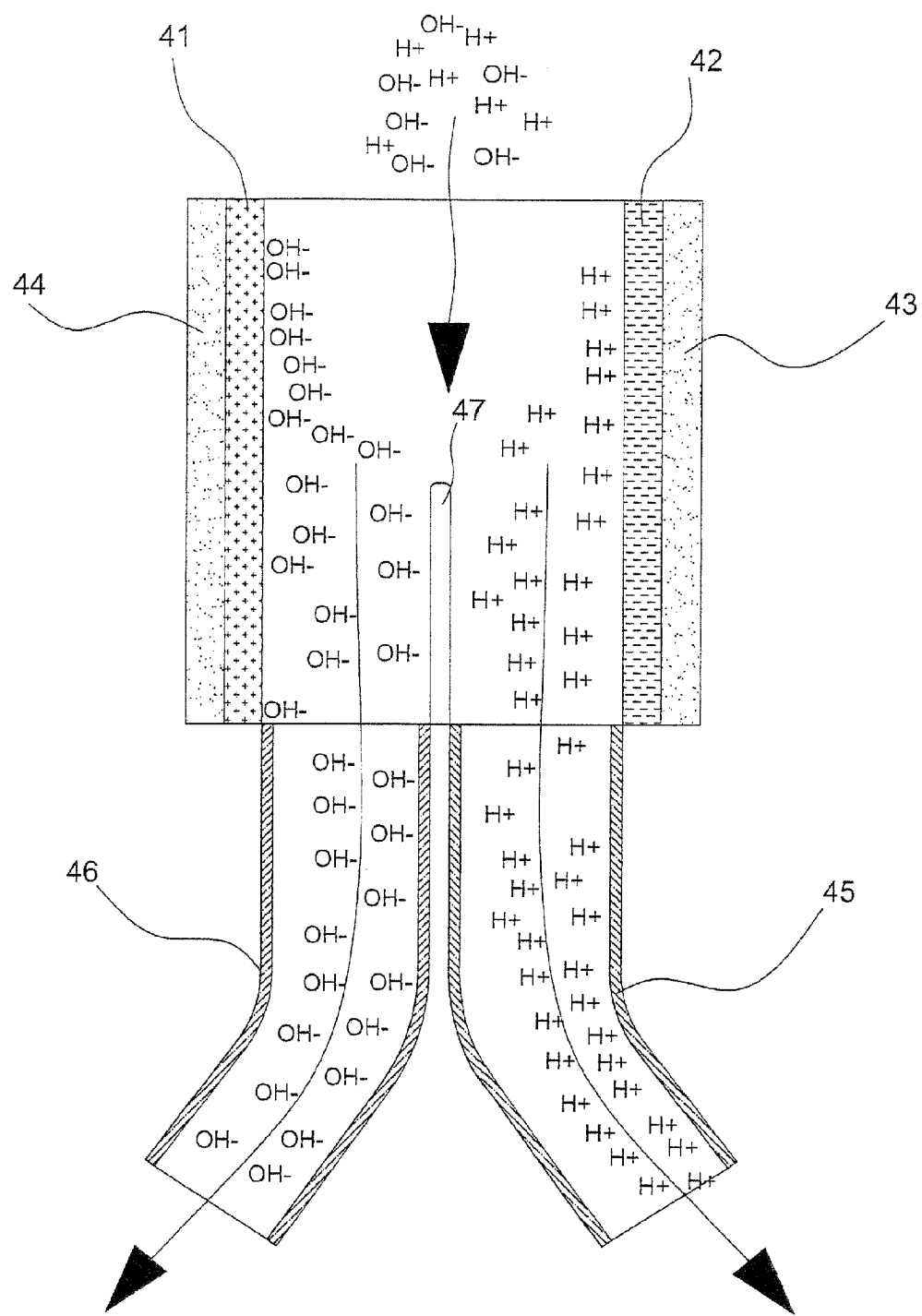
FIG. 4 shows a schematic view of an ion separation device in accordance with the present invention.

(b) Sequential to the previous step, an ion separation device 13 is employed to fast separate the H ions and the OH ions, as illustrated in FIG. 4. The ion separation device (see FIG. 4) comprises parallel electrical field and magnetic field for separation of hydrogen ions and hydroxide ions. The presence of the magnetic field causes spinning of electrons to reduce impedance and making in a condition similar to being fixed of voltages, leading to better efficiency.

(c) Sequential to the previous step, two conveyance tubes 45, 46 respectively connected to outlets of the ion separation device 13 are provided to respectively conduct the $H^+$ ions and $OH^-$ ions so separated to dissolve in pure water of different containers to respectively form alkaline green-energy water 15 that contains $H_3O_2^-$ and acidulous green-energy water 14 that contains $H_3O^+$, as shown in FIG. 1.

Figure 2:
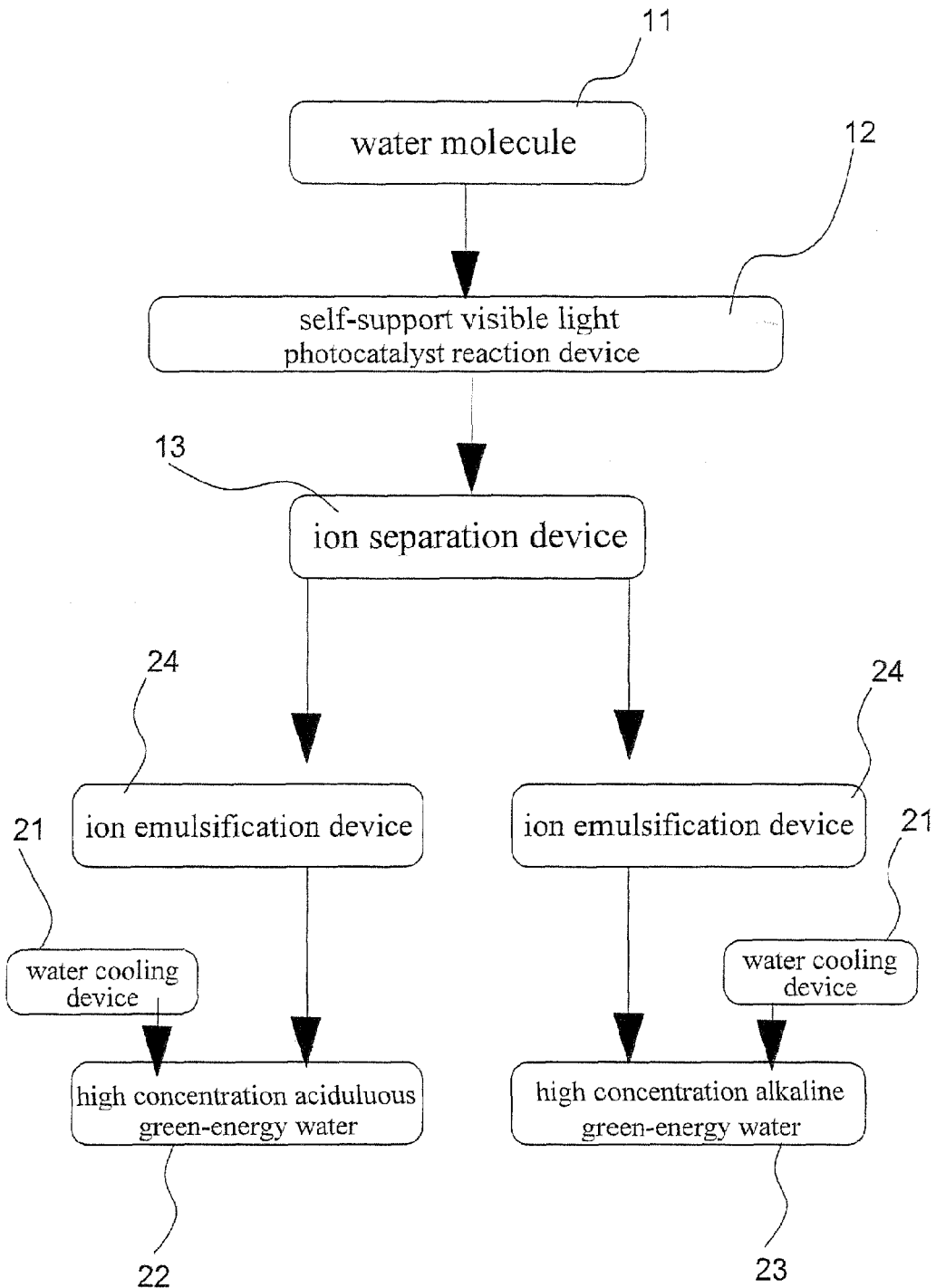
FIG. 2 shows a flow chart of a method for manufacturing green-energy water in accordance with a preferred embodiment of the present invention.
Figure 5:
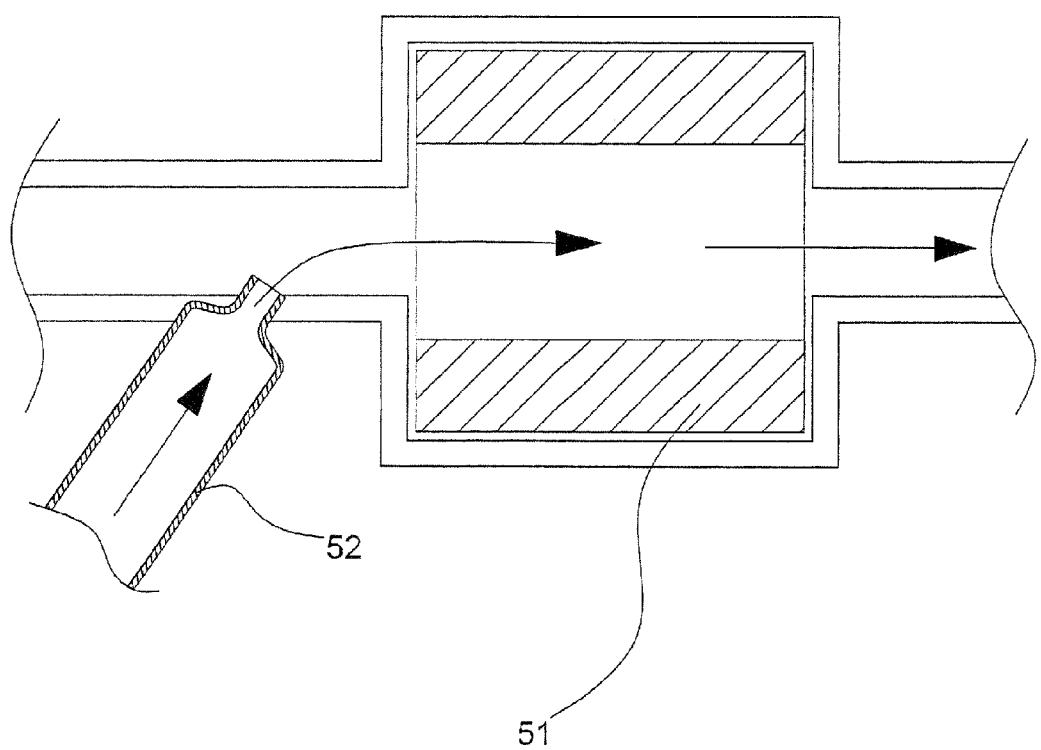
FIG. 5 shows a schematic view of an ion emulsification device in accordance with the present invention.

(d) In the previous step, the $H^+$ ions and $OH^-$ ions so separated can be respectively conducted by the conveyance tubes 45, 46 to pass through an ion emulsification device 24 for efficient dissolution in cold water to eventually form high concentration green-energy waters, as shown in FIGS. 2 and 5.

In a detailed example of the method for manufacturing green-energy water in accordance with the present invention, the following process is carried out:

(1) A heater 31 is activated to heat the visible-light photocatalyst board 34 to a temperature of about 60° C. for subsequent use. A light source 32 is turned on to irradiate visible light to a surface of the visible-light photocatalyst board 34 and the visible-light photocatalyst board 34, upon receiving the light wave, immediately performs an up-hill reaction (also referred to as accumulation of energy). The up-hill reaction shows a variation of free energy (which is generally denoted as "G") as follows: $\Delta G>0$, meaning a reaction of positive variation of free energy.

(2) Water molecules 11 are supplied to the self-support visible-light photocatalytic reaction device 12 and the water molecules 11 are decompose by the photocatalysts carried on the visible-light photocatalyst board 34 into $H^+$ ions and $OH^-$ ions, which are then fast conveyed to the next step.

(3) The $H^+$ ions and $OH^-$ ions enter an ion separation device (as shown in FIG. 4), wherein the H ions are attracted by a negative electrode 42 and an N magnetic pole 43, while the $OH^-$ ions are attracted by a positive electrode 41 and an S magnetic pole 44, so as to separate from each other and pass through an ion separation plate 47.

The separated hydrogen ions and hydroxide ions are respectively guided into the conveyance tubes 45, 46, whereby the hydrogen ions are conducted through the conveyance tube 45 that is close to the negative electrode 42 to an ion emulsification device 24 for emulsification and dissolution in water thereby forming acidulous green-energy water 14. The hydroxide ions are conducted through the conveyance tube 46 that is close to the positive electrode 41 to an ion emulsification device 24 for fast emulsification and dissolution in water thereby forming alkaline green-energy water 15.

Further, in the green-energy water manufacturing method of the present invention, water serves as a heterogeneous solute. If water can contain aqueous solute and the pH value of aqueous solute is made corresponding to the pH value of the $H^+$ ions or $OH^-$ ions that is conducted into the water, then the activity of the hydrogen ions and hydroxide ions in water can be lowered and the concentration of the green-energy water can be increased. Thus, it is preferable to allow the hydroxide ions to dissolve in an aqueous solution containing base radicals and allow the hydrogen ions to dissolve in an aqueous solution containing acid radicals in order to extends the lifespan of the ions and thus increase the concentration of the green-energy water.

In a preferred embodiment of the present invention, the separated hydrogen ions are conducted by the conveyance tube 45 through a Venturi tube 52 into the ion emulsification device 24. Before the ion emulsification device 24 is put into operation, a water cooling device 21 is started up first to cool down the water contained in the ion emulsification device 24, by which the water temperature is lowered to about 4° C. above the freezing point, in order to increase the half-life period of the hydrogen ions and make the ions fast dissolving in the cold water to form high concentration acidulous green-energy water 22. The separated hydroxide ions are conducted by the conveyance tube 46 through a Venturi tube 52 into the ion emulsification device 24 for fast emulsification and dissolution into water. Again, before the ion emulsification device 24 is put into operation, a water cooling device 21 is started up first to cool down the water contained in the ion emulsification device 24, by which the water temperature is lowered to about 4° C. above the freezing point, in order to form high concentration alkaline green-energy water 23.

It can be known from the above description of the manufacturing method that the green-energy water manufacturing device in accordance with the present invention comprises: a self-support visible-light photocatalytic reaction device 12, an ion separation device 13, and an ion emulsification device 24. With the green-energy water manufacturing device performing the above discussed manufacturing method, alkaline green-energy water 15 that contains $H_3O_2^-$ and/or acidulous green-energy water 14 that contains $H_3O^+$ can be manufactured. The self-support visible-light photocatalytic reaction device 12 provides energy for decomposition of water, as illustrated in FIG. 3. The ion separation device 13 contains parallel electrical field and magnetic field for separation of hydrogen ions and hydroxide ions, as illustrated in FIG. 4.

In a most preferred embodiment of the method for manufacturing green-energy water in accordance with the present invention, water molecules are decomposed by the visible-light photocatalytic reaction device and is then separated by ion separation device 13, whereby hydrogen ions and hydroxide ions separated by the ion separation device 13 are fed into pure water of a temperature above the freezing point and is conducted through a Venturi tube into a ion emulsification device 24 for fast dissolution to form high concentration green-energy water. In a second most preferred embodiment, water molecules are subjected to decomposition by the visible-light photocatalytic reaction device and separation by the ion separation device 13 and ions that are separated by the ion separation device 13 are respectively conducted into water to form green-energy water.

A detailed embodiment of the self-support visible-light photocatalytic reaction device 12 (see FIG. 3) will be described. The self-support visible-light photocatalytic reaction device 12 comprises a visible-light photocatalyst board 34, a light source 32, and a heater 31.

The visible-light photocatalyst board 34 is formed by employing vacuum physical vapor deposition (PVD) or chemical vapor deposition (CVD) to coat visible-light photocatalysts $TiO_xN_{1-x}$ on a metal or mesh-like substrate. The visible-light photocatalyst board 34 is thus formed in this way. The visible light photocatalyst has a reduced energy gap so that it can absorb the visible light and realize sufficient ability of oxidation and reduction through stepwise transition. Thus, the visible light photocatalyst may improve the efficiency. Since the photocatalyst is powered by light, it is involved with transmission and bandwidth of light. The ultraviolet light that has a short wavelength causes a great loss in transmission through space so that the ultraviolet light takes only a very limit fraction in the surface of the earth. However, if the bandwidth is extended to visible light, then the amount of light quantum that can excite photocatalysts can be increased and the efficiency is thus improved and secondary light pollution can be avoided.

Clearly, the visible light can easily transmit through the space and show a wider spectrum and thus using visible light to excite photocatalysts provide much more electrons than using ultraviolet light to excite photocatalysts. In addition, a heater 31, which can be any of various types, including an infrared type, thermal electron type, or electrical resistance type, is applied to realize heating to a temperature lower than 100° C., and further, a light source 32 is provided to excite the photocatalyst for decomposing $H_2O$, suiting the above discussed mechanism of $\Delta G>0$ up-hill reaction for photocatalyst based decomposition of $H_2O$. In a preferred embodiment, the visible-light photocatalyst board 34 is further connected to a metal wire serving as a grounding line 33 that is grounded to provide a route for discharging electrons thereby improving the separation of electrons and holes and enhancing the reaction efficiency of the photocatalyst.

The heater 31 can be a heating device of any one of a number of heaters, including infrared heater, thermal electron heater, and electrical resistance heater and functions for realizing heating to a temperature less than 100° C. With the heater 31 maintaining the temperature of the reaction environment within a range lower than 100° C., the efficiency of water decomposition is enhanced. This is because larger reaction activity and surface are provided for forming hydroxide ions and hydrogen ions, thereby enhancing activity of catalyzed photoreaction and sensitized photoreaction and thus enhancing the optimum efficiency of photocatalyst for decomposing water.

The light source 32 irradiates visible light to the visible-light photocatalyst board 34 for exciting the photocatalyst. When the photocatalyst is excited (having a reaction formula:

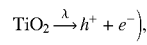

$$TiO_2 \xrightarrow{\lambda} h^+ + e^-),$$

the electrons are affected by the grounding line 33 to fast separate. The holes on the surface of the photocatalyst reacts with water to cause a $\Delta G>0$ up-hill reaction mechanism, making water decomposed (showing a reaction formula: $h^+ + 2H_2O \rightarrow OH^- + H_3O^+$).

A detailed embodiment of the ion separation device 13 (see FIG. 4) will be described. The ion separation device 13 in accordance with the present invention, as shown in FIG. 4, comprises an inlet end, an outlet end, an electric field, a magnetic field, an ion separation plate 47, and two conveyance tubes 45, 46.

The inlet end allows water entrained with $H^+$ and $OH^-$ ions to flow into the ion separation device.

The outlet end is set opposite to the inlet end and allows processed water to flow out of the ion separation device.

The electric field is composed of a positive electrode board 41 and a negative electrode board 42 opposite to the positive electrode board 41 and a direct current (DC) is applied to the electric field.

The magnetic field is set parallel to the electric field and is composed of an N pole 43 and an S pole 44. The N pole 43 and the S pole 44 are opposite to each other and are spaced by a predetermined distance.

The ion separation plate 47 is arranged midway between the positive electrode board 41 and the negative electrode board 42 for separation of $H^+$ ions and $OH^-$ ions.

The two conveyance tubes 45, 46 are connected to the outlet end of the ion separation device and are respectively set on opposite sides of the ion separation plate 47 to respectively receive and convey $H^+$ ions and $OH^-$ ions.

In the operation of the ion separation device 13, $OH^-$ and $H^+$ generated by the self-support visible-light photocatalytic reaction device 12 are conducted through the parallel arranged electric field device and magnetic field device. $OH^-$ is attracted by the positive electrode/pole, while the $H^+$ is attracted by the negative electrode/pole, and they are thus separated. The separated $H^+$ is conducted out through the conveyance tube 46 and $OH^-$ is conducted through the other conveyance tube 45 so as to realize separation of the ions.

The ion separation device 13 provides a function for preventing the occurrence of reversed reaction and is coupled to the self-support visible-light photocatalytic reaction device 12 and comprises an electric field composed of a DC power source and positive and negative electrodes 41, 42, a magnetic field composed of opposite N and S poles 43, 44, an ion separation plate 47, and conveyance tubes 45, 46 for conveyance of ions. The ion separation device 13 that is so composed of the four components helps fast separation of ions and prevents reversed reaction occurring on the ions.

A detailed embodiment of the ion emulsification device 24 will be described. The ion emulsification device 24 of the present invention, as shown in FIG. 5, is connected to the conveyance tubes 45, 46 of the ion separation device 13 and comprises a Venturi tube 52 and an ultrasonic wave emission source 51.

The Venturi tube 52 is connected to the ion separation device 13, so that each of the two conveyance tubes 45, 46 is coupled to one Venturi tube 52.

The ultrasonic wave emission source 51 is arranged in a flow channel and is connected to the Venturi tube 52 through the flow channel. When $OH^-$ ions are conducted from the conveyance tube 46 through the Venturi tube 52 into water and thus flowing into the flow channel, oscillation caused by the ultrasonic wave emission source 51 increases the collision frequency between the ions and water thereby inducing fast emulsification and dissolution to form high concentration alkaline green-energy water 23. When $H^+$ ions are conducted from the conveyance tube 45 through the Venturi tube 52 into water and thus flowing into the flow channel, oscillation caused by the ultrasonic wave emission source 51 increases the collision frequency between the ions and water thereby inducing fast emulsification and dissolution to form high concentration acidulous green-energy water 22, and high concentration alkaline green-energy water 23. The dissolution of H and OH ions of gas phase into water of liquid phase concerns about physical properties thereof and collision frequency therebetween. The higher the collision frequency is, the shorter the time needs for dissolution and a greater the amount of dissolution is. Thus, employing the principle of Venturi tube to conduct the gaseous H or OH ions into water and further employing the ultrasonic vacuum effect to attract the H and OH ions for extending the time they stay in water, together with the fast collision between the gas and liquid phases caused by sonic wave, fast emulsification can be realized to form high concentration green-energy water.

In the present invention, the $H_3O_2^-$ green-energy water that contains $OH^-$ has a pH value that is great, making it alkaline and possessing high activation energy, so that it is capable to decompose both saturated and non-saturated organic substances into $H_2O$ and $CO_2$. It can be used to manufacture green-energy water that contains only a very limited amount of organic substances, to manufacture green-energy water that can be used to remove TOC from waste water, or to clean semiconductor and optic substrates. The $H_3O_2^-$ green-energy water contains base radicals that may neutralize acids and can thus be used to neutralize soils that are getting acidified or serve as functional water for agriculture and cultivation for applications in ecological engineering for handling contaminated soils and cleaning waste water.

The $H_3O^+$ green-energy water that contains $H^+$ has a pH value that is small, making is acidulous and possessing high activation energy, so that it can decompose harmful substances that cannot be decomposed by chlorine and ozone and exhibits the characteristics of sterilization, deodorization, decolorization, and metal oxidization, and can be used in cleaning of semiconductor and optic substrates, cleaning of medical equipments, and purification of water.

The efficacy of the present invention is as follows.

(1) The method for manufacturing green-energy water in accordance with the present invention starts with a primitive raw material of water and when the water becomes ions to participate in chemical reaction, energy is released and it turns back to water, leaving completely no secondary pollution.

(2) The present invention provides a $\Delta G>0$ up-hill reaction with which photocatalyst decomposes water, whereby the reaction rate is increased and the green-energy water can be manufactured with great productivity to allow expansion of the applications thereof and provide a practical solution for green technology.

(3) The present invention provides an internal electrically-conductive metal that forms a focus for accumulation of electrons, providing excellent attraction to electrons of $TiO_2$, and grounding that discharges electrons to make fast separation of electrons and holes, inducing simultaneously catalyzed photoreaction and sensitized photoreaction to allow for increase of efficiency for fast generation of green-energy water.

(4) Regular photocatalysts only provide a two-dimensional application on the contact surface, but the present invention makes green-energy water that allows for expansion of their application to a three-dimensional range. (Two-dimension means the photocatalysts provide a passive reaction with substance in contact with a surface thereof and three-dimension means the green-energy water actively seeks for substances that can react with it, and it provides such an active effect for reaction in a three-dimensional space due to water being a substance that shows co-existence of gas phase and liquid phase.)

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A method for manufacturing green-energy water, comprising: conducting water flow through a self-support visible-light photocatalytic reaction device, which decomposes the water into hydrogen ions and hydroxide ions; conducting the hydrogen ions and the hydroxide ions through an ion separation device, which separates the hydrogen ions and the hydroxide ions from each other; and conducting the separated hydroxide ions into an amount of water to form an amount of alkaline green-energy water and conducting the separated hydrogen ions into another amount of water to form an amount of acidulous green-energy water, wherein the hydroxide ions are dissolved in an aqueous solution containing base radicals and the hydrogen ions are dissolved in an aqueous solution containing acid radicals, in order to form high concentration green-energy water.

2. The method according to claim 1, wherein the hydrogen ions and the hydroxide ions, after being separated by the ion separation device, are subjected to processing comprising the following steps: employing a water cooling device to reduce temperature of water flowing through an ion emulsification device; and conducting the separated hydrogen ions into the water of the ion emulsification device to form high concentration acidulous green-energy water; and conducting the separated hydroxide ions into the water of the ion emulsification device to form high concentration alkaline green-energy water.

3. The method according to claim 1, wherein the hydroxide ions are dissolved in an aqueous solution containing base radicals and the hydrogen ions are dissolved in an aqueous solution containing acid radicals, in order to form high concentration green-energy water.

4. A green-energy water manufacturing device comprising: a self-support visible-light photocatalytic reaction device; and an ion separation device coupled to the self-support visible-light photocatalytic reaction device, wherein the ion separation device comprises: an inlet end, an outlet end, an electric field, which is supplied with a direct current and comprises a positive electrode board, and a negative electrode board opposite to the positive electrode board; an ion separation plate, which is set between the positive and negative electrode boards; and two conveyance tubes, which are connected to the outlet end of the ion separation device and are respectively located at opposite sides of the ion separation plate.

5. The green-energy water manufacturing device according to claim 4, further comprising an ion emulsification device, which is connected to the ion separation device and comprises an ultrasonic wave emission source for emulsifying the ions.

6. The green-energy water manufacturing device according to claim 4, wherein the self-support visible-light photocatalytic reaction device comprises: a visible-light photocatalyst board, a heater, a light source, and a grounding line.

7. The green-energy water manufacturing device according to claim 4, wherein the ion separation device comprises: an electric field, which is supplied with a direct current and comprises a positive electrode board and a negative electrode board opposite to the positive electrode board; a magnetic field, which is set parallel to the electric field and comprises an N magnetic pole and an S magnetic pole; an ion separation plate, which is set between the positive and negative electrode boards; and two conveyance tubes, which are respectively located at opposite sides of the ion separation plate for respectively conveyance of the hydrogen ions and the hydroxide ions.

8. The green-energy water manufacturing device according to claim 4, wherein the hydroxide ions that are separated by the ion separation device are conducted through a Venturi tube that is connected to the ion separation device into the ion emulsification device, the ultrasonic wave emission source of the ion emulsification device emitting ultrasonic waves to the hydroxide ions to cause emulsification and thus fast dissolution of the hydroxide ions into water to thereby form high concentration alkaline green-energy water; the water conducted into the Venturi tube being cooled by a water cooling device to have temperature of the water controlled within a range between freezing point and room temperature.

9. The green-energy water manufacturing device according to claim 4, wherein the visible-light photocatalyst board comprises a metal mesh.

10. The green-energy water manufacturing device according to claim 4, wherein the heater is a heating device selected from a group consisting of electrical resistance heater, infrared heater, and thermal electron heater.

* * * * *